US010918508B2

(12) United States Patent
Milisav et al.

(10) Patent No.: US 10,918,508 B2
(45) Date of Patent: Feb. 16, 2021

(54) RELEASE SYSTEM FOR A SELF-EXPANDING ENDOPROSTHESIS

(71) Applicant: BENTLEY INNOMED GMBH, Hechingen (DE)

(72) Inventors: Obradovic Milisav, Lörrach (DE); Obradovic Aleksandar, Lörrach (DE)

(73) Assignee: Bentley Innomed GMBH, Hechingen (DE)

( * ) Notice: Subject to any disclaimer, the term of this patent is extended or adjusted under 35 U.S.C. 154(b) by 154 days.

(21) Appl. No.: 16/075,446

(22) PCT Filed: Feb. 9, 2017

(86) PCT No.: PCT/EP2017/052810
§ 371 (c)(1),
(2) Date: Aug. 3, 2018

(87) PCT Pub. No.: WO2017/137471
PCT Pub. Date: Aug. 17, 2017

(65) Prior Publication Data
US 2019/0038442 A1 Feb. 7, 2019

(30) Foreign Application Priority Data
Feb. 9, 2016 (DE) ...................... 10 2016 102 212.8

(51) Int. Cl.
*A61F 2/962* (2013.01)
*A61F 2/97* (2013.01)
(Continued)

(52) U.S. Cl.
CPC ................ *A61F 2/962* (2013.01); *A61F 2/92* (2013.01); *A61F 2/958* (2013.01); *A61F 2/966* (2013.01); *A61F 2/97* (2013.01); *A61F 2/07* (2013.01)

(58) Field of Classification Search
CPC .. A61F 2/962; A61F 2/92; A61F 2/958; A61F 2/966; A61F 2/97; A61F 2002/9665
See application file for complete search history.

(56) References Cited

U.S. PATENT DOCUMENTS

| 8,641,752 B1 | 2/2014 | Holm |
|---|---|---|
| 2004/0143315 A1 | 7/2004 | Bruun |

(Continued)

FOREIGN PATENT DOCUMENTS

| RU | 201414141051 A | 4/2016 |
|---|---|---|
| WO | 2013137978 A1 | 9/2013 |

OTHER PUBLICATIONS

Russian Patent Authority Office Action for RU 2018131925 (machine translation English), dated Apr. 15, 2020.

*Primary Examiner* — Katrina M Stransky
(74) *Attorney, Agent, or Firm* — Wuersch & Gering LLP

(57) ABSTRACT

The invention relates to a release system for a self-expanding endoprosthesis, comprising a catheter, an endoprosthesis (2) having a first volume-reduced shape under an external constraint and, after elimination of the external constraint, assuming a second expanded shape at the placement site and being movably arranged in the catheter, a means for holding (6, 7) the endoprosthesis (2) in the catheter as well as means suitable to exert the external force on the endoprosthesis (2), wherein the means for exerting the external force on the endoprosthesis (2) is a tubular film (3) whose distal end encloses the endoprosthesis (2) in its reduced-volume form and whose proximal end extends to the proximal end of the catheter in such a way that it can be withdrawn from the endoprosthesis (2) thus eliminating the external constraint.

23 Claims, 3 Drawing Sheets

(51) Int. Cl.
*A61F 2/966* (2013.01)
*A61F 2/92* (2013.01)
*A61F 2/958* (2013.01)
*A61F 2/07* (2013.01)

(56) References Cited

U.S. PATENT DOCUMENTS

| | | |
|---|---|---|
| 2005/0182384 A1 | 8/2005 | Kantor |
| 2006/0015171 A1 | 1/2006 | Armstrong |
| 2008/0255580 A1* | 10/2008 | Hoffman .................. A61F 2/95 606/108 |
| 2010/0049297 A1 | 2/2010 | Dorn |
| 2011/0118817 A1* | 5/2011 | Gunderson .............. A61F 2/95 623/1.12 |
| 2012/0059448 A1* | 3/2012 | Parker ...................... A61F 2/95 623/1.11 |
| 2012/0143303 A1* | 6/2012 | Dorn ....................... A61F 2/966 623/1.12 |

* cited by examiner

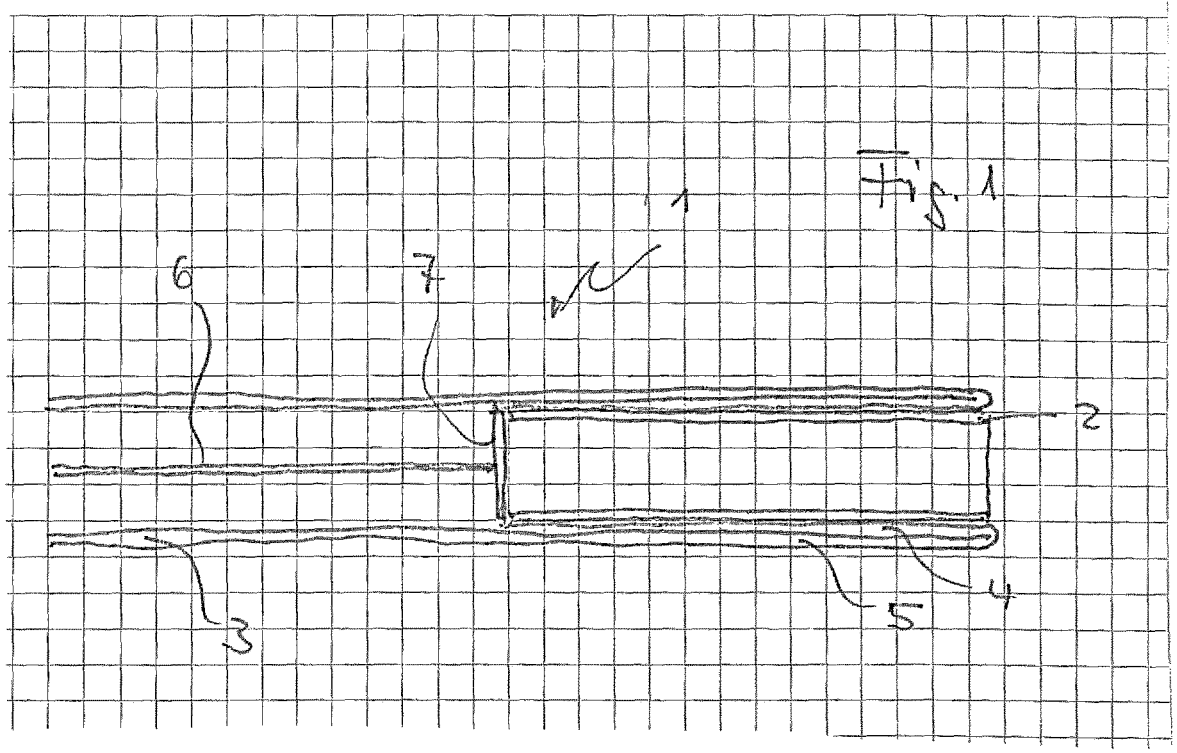
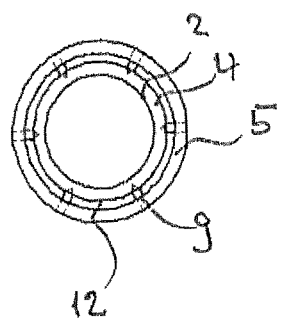
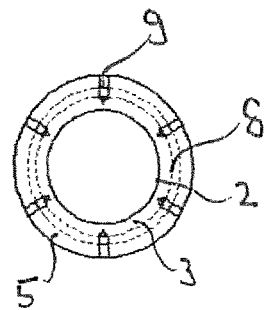

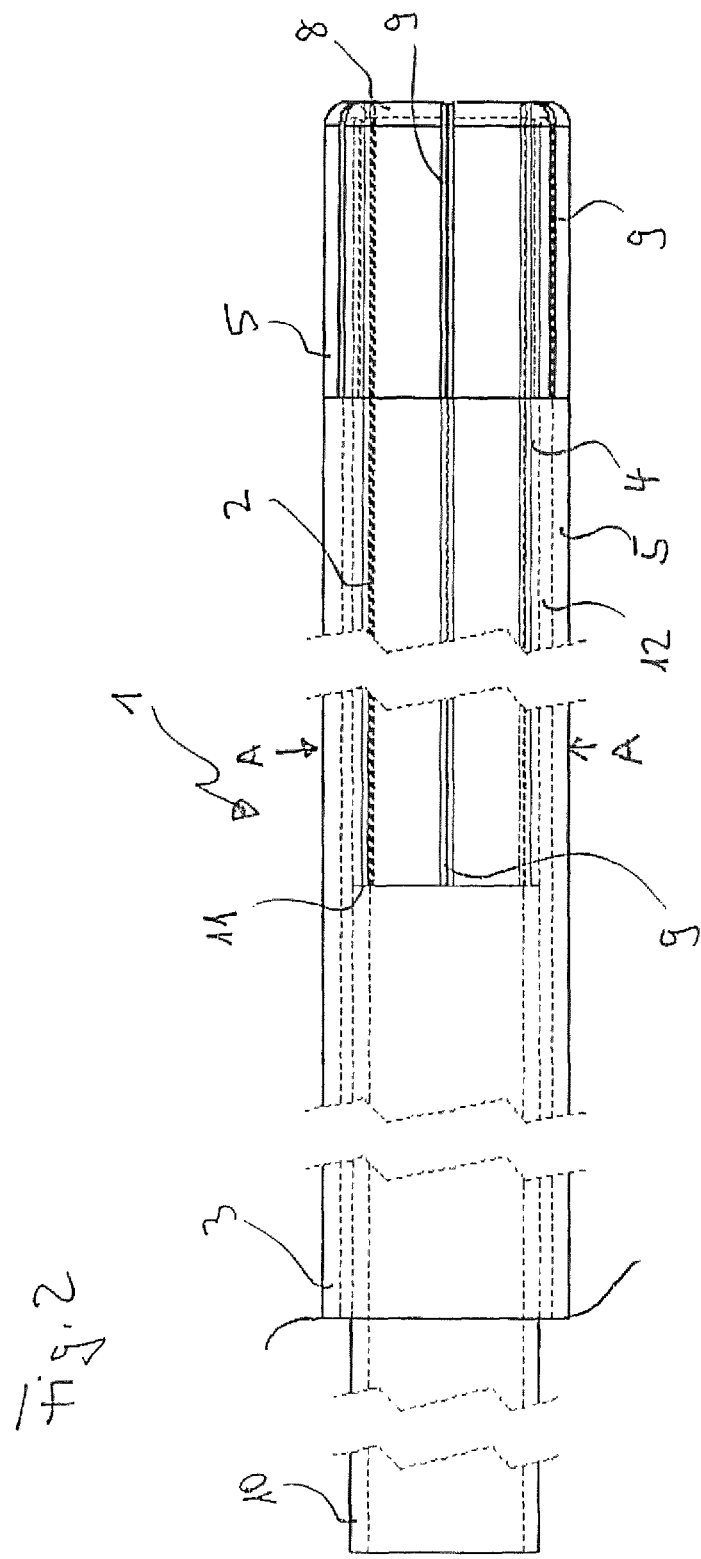

RELEASE SYSTEM FOR A SELF-EXPANDING ENDOPROSTHESIS

The invention relates to a release system for a self-expanding endoprosthesis, said system comprising a catheter, an endoprosthesis which under external constraint has a first volume-reduced shape and, when the external constraint is removed, takes on a second expanded shape at the placement location and is movably arranged in the catheter, a means for holding the endoprosthesis in the catheter as well as a means suitable for exerting the external constraint on the endoprosthesis. The endoprosthesis is especially a vascular stent.

Endoprostheses, in particular stents for the vascular system, are known in a variety of forms. As regards stents, a distinction is made between balloon-expandable stents and self-expanding stents. Both variants are implanted using catheters especially designed for this purpose. During implantation, it is very important that the stent is exactly positioned in the required place. In this context a problem arises in particular with longer self-expanding stents, which are often inserted peripherally.

Self-expanding stents are made of a shape memory alloy, such as nickel-titanium alloys (nitinol), and are caused to assume a first reduced-volume form as required for placement in the catheter, i.e. they have a reduced diameter. In the catheter they maintain this reduced diameter due to the external constraint exerted by the catheter tube. As they are pushed out of the catheter, these stents then take on their second expanded form having an enlarged diameter, which they retain at the implantation site. Since expansion occurs as soon as the stent leaves the catheter and due to the fact that these stents temporarily have an expanded distal end and a volume-reduced proximal end, and, moreover, friction forces become effective when the stents are released from the catheter, the precision of stent placement suffers. Such inaccuracies may even increase because the length of the expanding stent reduces when it exits the catheter.

Various techniques have been developed to address and solve this problem. One of these methods is based on the use of a mechanical placement aid by means of which the stent is pushed out of the catheter in a controlled manner. It is also known that the stent is enclosed in a sheath which is made to burst at the placement site with the aid of a balloon arranged in the stent; the stent is thus allowed to expand and the balloon is retracted out of the vascular system with the catheter. Both methods are constructively complex and sophisticated. When adopting the latter method, sheath material may even remain in the vascular system.

It is, therefore, the objective of the present invention to provide a release system for self-expanding endoprostheses, in particular stents, which allows the endoprosthesis to be released reliably and precisely at the placement site using simple means.

This objective is accomplished by proposing a release system of the kind first mentioned above, in which the means of exerting the external force on the endoprosthesis is a tubular film which encloses the endoprosthesis in its reduced-volume form and extends with its proximal end to the proximal end of the catheter such that it can be withdrawn from the endoprosthesis and in this way eliminates the external constraint.

The invention is described below by reference to a self-expanding stent held in the reduced-volume form by means of a tubular film.

The tubular film is an appropriate means of effectively embracing the stent. The tube can be withdrawn with little effort thus allowing the stent expand. It goes without saying that the stent must be held in position in the course of the release process by the retaining device, which may be an exposed pusher.

Preferably, the tubular film with its outer side is in contact distally with the stent, extends to the distal end of the stent at which location it is folded back (rolled up) on itself to run back along the stent to the proximal end of the catheter.

In particular, the tubular film starts at the proximal end of the stent, extends over the entire length of the stent in order to reverse at its distal end and return to the proximal end of the catheter. The tubular film thus provides a double covering over the entire length of the stent. The outer tube on which the tensile force acts can be made stronger and more stable than the part resting on and being in contact with the stent.

The tubular film, as used in the invention, is comparable to a sleeve that embraces the stent in its volume-reduced first form and holds it in position. To release the stent, the attending physician pulls it back through the catheter introducer sheath until the stent is released. Preferably, the stent's connection to the holding means also detaches at the same time as the stent is released.

The double covering of the stent by the tubular film offers the advantage that the stent can be withdrawn with very little effort. The material used for the tubular film, especially a medically compatible and unobjectionable plastic and preferably PTFE, has good sliding properties with respect to its own and other materials and, accordingly, its friction characteristics are low. This makes it easier to push the stent out of the catheter and initiate its release. Friction of the stent at and in contact with the catheter wall and compression of the stent as it is pushed out is a frequently occurring problem, especially with peripheral stents of greater length.

In order to facilitate the withdrawal of the tubular film, it can be provided with perforations and slots that cause the tubular film to tear open when it is retracted. These perforations or slots are conveniently arranged and extend along at least one longitudinal line. In this manner, tubular film portions which should not remain in the vasculature are prevented from tearing off.

It is also advisable to arrange perforations in the catheter in the distal area in which the stent is transported and to provide a flushing facility, which further increases the enveloped stent's tendency to slide inside the catheter. The flushing fluid can also penetrate to the enveloped stent through the perforations or slots arranged in the tubular film. In this context, the flushing liquid exerts a desired lubricating effect.

In addition, catheter, tubular film and/or stent may have a hydrophilic coating to improve lubricity. For catheters, such coatings are known per se.

To reduce friction between the film layers positioned on the stent during withdrawal, it may be helpful to arrange for perforations in the outer film layer to allow liquid to ingress. In contrast to any perforations intended to facilitate tearing of the film, these perforations are distributed over the surface.

As means provided for holding and displacing the stent a guidewire or pusher can be employed, each coupled to the stent or being located adjacent to the stent. After separation of the stent from the catheter, the holding function is required to hold the stent in position during the withdrawal/removal of the film. For example, the guidewire or pusher can engage from the inside with the meshes of the nonexpanded stent via an appropriately designed holding device at its distal end; this connection is severed when the stent is released and expanded.

A guidewire or pusher is preferred, which is connected to the stent via the tubular film and is separated from the stent by the withdrawal of the tubular film. For example, the distal end of the guidewire may be provided with a disc whose diameter corresponds to the diameter of the stent in its reduced-volume form and which reaches directly up to the stent. As soon as the tubular film is withdrawn/removed from the stent, the stent expands along its entire length and is separated from the guidewire or loses contact with the abutting pusher.

A separate tube suitable for holding the stent in position when the catheter is retracted and having a distal end extending to the proximal end of the stent can also be employed as a pusher element. For this purpose, the proximal end of this separate tube may be reinforced, of beaded shape or folded around to form an appropriate abutment for the stent. The separate tube extends coaxially inside the tubular film to the proximal end of the catheter and can be manipulated/controlled through the introducer sheath by the attending physician.

If the pusher is formed by a separate tube, it usually has a thicker wall than the tubular film so that it is capable of transmitting the thrust force required for the placement of the stent.

In accordance with another embodiment of the invention, the separate tube of the pusher can be connected to the tubular film that embraces the stent, for example by means of a welded connection. In this case, it connects to the distal end of the tubular film which is directly resting on the stent.

To minimize friction between the two layers of tubular film, i.e. the distal end of the tubular film arranged directly on the stent and the proximal part that runs back from the distal end of the stent to the proximal end of the catheter and is folded around onto the distal end of the tubular film, it considered expedient to arrange for the proximal part of the tubular film to be slightly wider in diameter than the distal end.

It is also possible to use a tube material of greater tensile strength for the section of the proximal part of the tubular film that extends beyond the length of the stent.

Other detachment mechanisms may also be used. For example, a mechanical attachment of the guidewire to the stent can be severed electrolytically in a known manner.

The terms "proximal" and "distal" used here are synonymous with "facing the attending physician or catheter end", respectively "facing away from the attending physician or catheter end".

The invention is explained in more detail by way of the enclosed figures showing preferred embodiments. It is to be understood that the features and characteristics shown there and described in more detail hereinafter can generally be read in relation to the invention described here and are not only related to the individual case described.

The following is shown in the figures, where

FIG. 1 is schematic and sectional view of a 1st variant of a release system in accordance with the invention;

FIG. 2 shows a 2nd variant of a release system proposed by the invention;

FIG. 3 is a sectional view along line A-A through the release system as per FIG. 2;

FIG. 4 shows the release system as per FIG. 2 seen from the front side;

Figure 5:
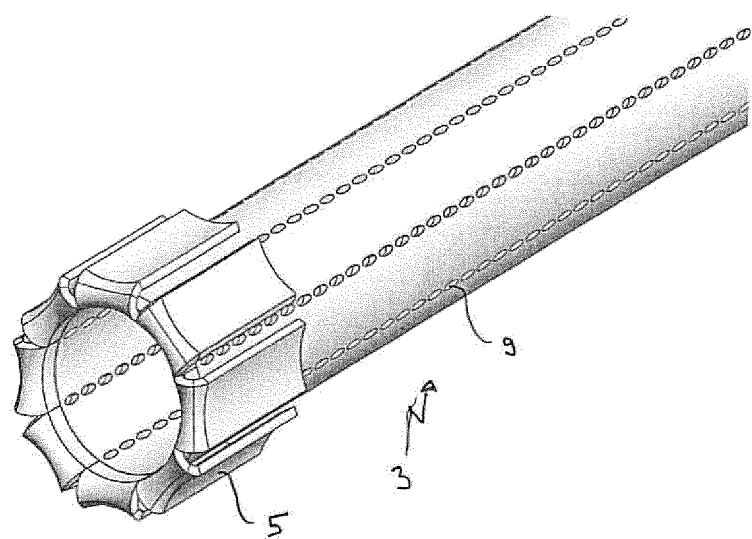
FIG. 5 shows the tubular film used for the fixation of a stent.

FIG. 1 shows a sectional view of a first variant of a release system 1 proposed by the invention in which a stent 2 is arranged within a tubular film 3. The tubular film 3 has a distal end 4 which rests directly on the stent 2 and holds it in its reduced-volume form. Stent 2 consists of a shape memory material, preferably a nickel-titanium alloy, such as nitinol, which is held in its reduced-volume form as a result of external constraint exerted. The external constraint or pressure is exerted by the tubular film 3.

Tubular film 3 is divided into the distal part 4 and the proximal part 5, wherein the distal part rests directly on and encloses the stent and the proximal part 5 is folded over onto the distal part 4 and extends back to the proximal end of the catheter (not shown). The catheter encloses the combination of stent 2 and tubular film 3.

To liberate the stent 2 from the catheter, a pusher is arranged at its proximal end. In the case shown, the pusher consists of a pusher wire 6 and a disc 7 abutting the proximal end of stent 2. Making use of the pusher wire 6 and disc 7, the force required to hold the stent 2 in position when the catheter is retracted can be exerted on the stent 2.

The release of stent 2 is achieved by pulling off the tubular film 3, and because the proximal end 5 of the tubular film is folded back onto the distal end 4, the entire tubular film 3 can be easily withdrawn and removed from the stent 2. The withdrawal can be facilitated by the arrangement of perforations, slots or weakening zones that extend in the longitudinal direction. In this case, the stent 2 can be exposed and released, just like peeling a banana.

In the case shown, stent 2 and disc 7 of the pusher are not connected with each other and are only held together by the tubular film 3. As soon as the tubular film 3 has been completely withdrawn and removed from the stent 2, the stent 2 expands and separates from disc 7 of the pusher.

FIG. 2 shows another variant of an inventive release system 1. The distal end 4 of the tubular film 3 holds the stent 2 in its reduced-volume form. As illustrated in FIG. 1, the proximal end 4 of the tubular film 3 has been folded back onto the distal part 2. Reference numeral 8 denotes the folding area of the tubular film, the reference numeral 9 defines longitudinally extending slots arranged on the tubular film 3 in the area of the stent 2, which facilitate tearing and retraction of the film. In general, such weaknesses of the tubular film are only provided in the area that covers the stent 2.

The tubular film 3 extends over the entire length of the catheter (not shown here) and can be withdrawn from stent 2 by the attending physician via its end projecting out of the introducer sheath.

In the case shown, the pusher consists of a hose or flexible tube 10 running inside the tubular film 3. Tube 10 is sufficiently rigid to transmit the force required for the separation of the stent 2 from the catheter. Tube 10 is attached by welding at 11 to the distal end of distal part 4 of tubular film 3. All tubes and tube components extend coaxially.

Between the distal part 4 of tubular film 3, which rests directly on stent 2, and its folded-back proximal part 5 there is a clearance 12, which results from the different diameters of the tubular film portions. This reduces friction and facilitates "peeling" the film off.

FIG. 3 shows a cross section A-A through the release system illustrated in FIG. 2. The figure shows the layered structure comprising the stent 2 located inside, the part 4 of the tubular film arranged on the stent, the clearance 12 existing between the two layers of tubular film and the tubular film 5 extending back in proximal direction on the outside. Slots 9 can also be seen, which make it easier to tear the tubular film 3 open during its retraction.

FIG. 4 is a front view of the distal end of the insertion device 1 showing the folding area 8 of the tubular film, the stent 2 located inside and the slots 9, through which the returning proximal end 5 of the tubular film 3 can be seen.

FIG. 5 depicts as isolated representation tubular film 3 with 8 perforation lines 9, evenly distributed over the circumference and extending in the longitudinal direction, which enable the tubular film 3 to be torn open. In case of application, the endoprosthesis 2 is located inside the tubular film 3 and the application catheter or tube is located on the outside. The tubular film 3 is folded around at its end and forms individual tongues 5. The incisions provided between the tongues 5 are in parallel alignment with the perforation lines 9, so that when the tubular film is withdrawn via the tongues 5, the tubular film tears open along the perforation line 9 causing the endoprosthesis embraced by the film, usually a self-expanding stent, to be released. To enable the tubular film 3 to be pulled back, a tube/hose (not shown) for example is arranged on the tongues. In lieu of the withdrawal tube/hose, cords or wires may as well be employed for instance.

The tubular film 3 preferably consists of PTFE, a material that provides low frictional resistance and thus facilitates the retraction of the tube.

Figure 6:
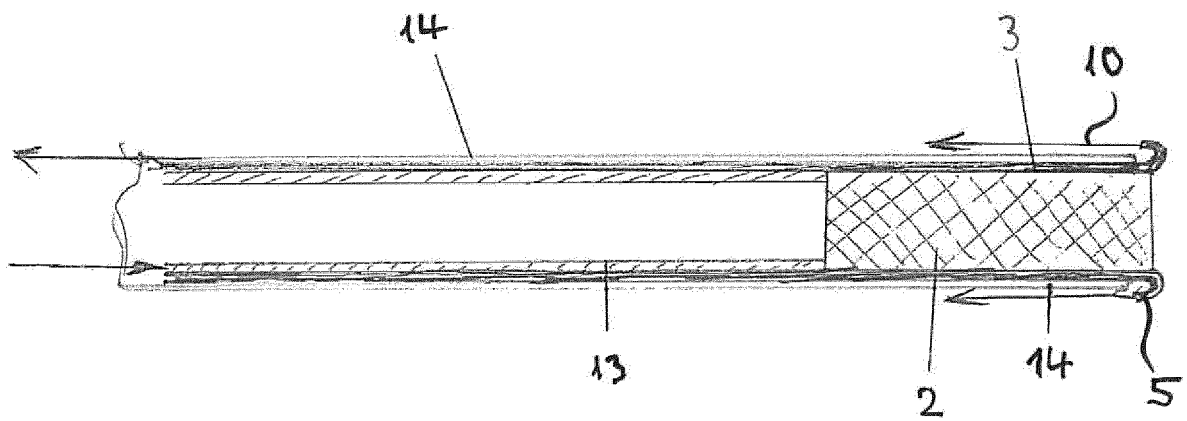
FIG. 6 is a schematic illustration of the inventive release system.

FIG. 6 shows the principle of the system in accordance with the invention comprising a stent 2, the tubular film 3 arranged on it, which is folded around at the distal end of the stent and terminates in the tongues 5, a pusher 13, which is suitable for pushing the stent out of the surrounding catheter or stabilization tube 14, as well as a tube 10 attached to the folded end 5 (corresponding to the tongues 5 in FIG. 5) for the withdrawal of the tubular film 3 from the stent 2 after release of the stent 2 from the catheter 14 with the aid of the pusher 13. Instead of tube 10, one or several traction cables may also be used.

In the illustration, the arrows indicate the direction of movement of the respective elements during placement of the stent 2.

The invention claimed is:

1. A release system for a self-expanding endoprosthesis, comprising:
    a catheter having a proximal end and a distal end;
    a pusher for holding an endoprosthesis;
    wherein the endoprosthesis is movably arranged in the catheter and has a first contracted shape when an external constraint is present and a second expanded shape when the external constraint is removed; and
    a tubular film to exert said external constraint on the endoprosthesis, said tubular film having a distal end portion and a proximal end portion, wherein the distal end portion of the tubular film encloses the endoprosthesis in the first contracted shape and the proximal end portion of the tubular film extends is folded over the distal end portion and extends towards the proximal end of the catheter in such a way that the tubular film can be withdrawn from the endoprosthesis at a placement site via the proximal end portion thereby eliminating said external constraint, and wherein the distal end portion of said tubular film is in contact with the endoprosthesis, extends to the distal end of the endoprosthesis, and further comprises perforations arranged along at least one longitudinal line that cause the tubular film to tear open along said perforations when it is withdrawn via the proximal end portion.

2. The release system of claim 1, wherein the distal end portion of said tubular film is in contact with the proximal end of the endoprosthesis.

3. The release system of claim 1, wherein the endoprosthesis is a vascular stent.

4. The release system of claim 3, wherein the vascular stent is a peripheral vascular stent.

5. The release system of claim 1, wherein the tubular film comprises a biocompatible plastic material.

6. The release system of claim 5, wherein the biocompatible plastic material is a polytetrafluoroethylene (PTFE).

7. The release system of claim 1, wherein the catheter comprises perforations in the distal region.

8. The release system of claim 1, wherein the catheter, the tubular film, and/or the endoprosthesis have a hydrophilic coating.

9. The release system of claim 1, wherein the catheter is provided with a flushing device.

10. The release system of claim 1, wherein the pusher is arranged within the tubular film.

11. The release system of claim 10, wherein the pusher is attached to the endoprosthesis in a detachable manner and arranged within the tubular film.

12. The release system of claim 11, wherein the pusher is self-releasing.

13. The release system of claim 11, wherein the pusher is a tube or hose.

14. The release system of claim 11, wherein the pusher further comprises a pusher wire and a disc.

15. The release system of claim 1 wherein the perforations are perforation lines or slots.

16. The release system of claim 15, wherein a plurality of perforation lines or slots are evenly distributed over the circumference of the tubular film and extend longitudinally along the tubular film.

17. The release system of claim 16, wherein the distal end portion of said tubular film is in contact with the proximal end of the endoprosthesis.

18. The release system of any one of claim 16, wherein the endoprosthesis is a vascular stent.

19. The release system of claim 18, wherein the vascular stent is a peripheral vascular stent.

20. The release system of claim 15, wherein the distal end portion of said tubular film is in contact with the proximal end of the endoprosthesis.

21. The release system of claim 15, wherein the endoprosthesis is a vascular stent.

22. The release system of claim 21, wherein the vascular stent is a peripheral vascular stent.

23. The release system of claim 1 wherein said proximal end portion of said tubular film forms individual tongues in parallel alignment with the longitudinal perforation lines so that when the tubular film is withdrawn via the tongues the tubular film tears open along the perforation lines.

* * * * *

UNITED STATES PATENT AND TRADEMARK OFFICE
CERTIFICATE OF CORRECTION

PATENT NO. : 10,918,508 B2  
APPLICATION NO. : 16/075446  
DATED : February 16, 2021  
INVENTOR(S) : Milisav Obradovic and Aleksandar Obradovic It is certified that error appears in the above-identified patent and that said Letters Patent is hereby corrected as shown below:

In the Claims

Claim 1, Column 5, Line 57 replace "tubular film extends is folded over" with --tubular film is folded over--.

Signed and Sealed this  
Sixth Day of September, 2022

Katherine Kelly Vidal  
*Director of the United States Patent and Trademark Office*